US011318449B2

United States Patent
Liu et al.

(10) Patent No.: US 11,318,449 B2
(45) Date of Patent: May 3, 2022

(54) ACID-RESISTANT ALLOY CATALYST

(71) Applicants: Changchun Meihe Science and Technology Development Co., LTD, Jilin (CN); The Coca-Cola Company, Atlanta, GA (US)

(72) Inventors: Jing Liu, Changchun (CN); Hongbin Qi, Changchun (CN); Haiyu Ren, Atlanta, GA (US)

(73) Assignees: Changchun Meihe Science and Technology Development Co., LTD, Jilin (CN); The Coca-Cola Company, Atlanta, GA (US)

( * ) Notice: Subject to any disclaimer, the term of this patent is extended or adjusted under 35 U.S.C. 154(b) by 13 days.

(21) Appl. No.: 16/625,057

(22) PCT Filed: Jun. 22, 2018

(86) PCT No.: PCT/CN2018/092311
§ 371 (c)(1),
(2) Date: Dec. 20, 2019

(87) PCT Pub. No.: WO2018/233677
PCT Pub. Date: Dec. 27, 2018

(65) Prior Publication Data
US 2020/0215519 A1 Jul. 9, 2020

(30) Foreign Application Priority Data

Jun. 22, 2017 (CN) .......................... 201710481326.4

(51) Int. Cl.
*B01J 23/887* (2006.01)
*B01J 35/00* (2006.01)
*C22C 19/03* (2006.01)

(52) U.S. Cl.
CPC ....... *B01J 23/8875* (2013.01); *B01J 35/0046* (2013.01)

(58) Field of Classification Search
CPC .... B01J 23/8875; B01J 35/0046; C22C 19/03
USPC ......... 502/302, 310, 315, 322; 420/455, 460
See application file for complete search history.

(56) References Cited

U.S. PATENT DOCUMENTS

| 5,290,509 A * | 3/1994 | Furukawa ............ H01M 4/383 420/435 |
| 10,556,226 B2 * | 2/2020 | Liu ........................ C22C 19/03 |
| 11,104,629 B2 | 8/2021 | Liu et al. |
| 2017/0203283 A1 | 7/2017 | Liu et al. |

(Continued)

FOREIGN PATENT DOCUMENTS

| CN | 101199930 | | 6/2008 | |
| CN | 10 5521788 | * | 4/2016 | ............ B01J 23/835 |
| CN | 10 5523890 | * | 4/2016 | ............ B01J 23/888 |

(Continued)

OTHER PUBLICATIONS

International Search Report from PCT/CN2018/092311, dated Aug. 29, 2018.

*Primary Examiner* — Patricia L. Hailey
(74) *Attorney, Agent, or Firm* — King & Spalding

(57) ABSTRACT

An acid-resistant alloy catalyst, comprising nickel, one or more rare earth element, tin, aluminum and molybdenum. The catalyst is cheap and stable, does not need a carrier, can be stably applied in industrial continuous production, and can lower the production cost.

5 Claims, 1 Drawing Sheet

(56) References Cited

U.S. PATENT DOCUMENTS

2017/0210687 A1 7/2017 Liu et al.
2019/0112248 A1* 4/2019 Yuan ...................... B01J 23/888

FOREIGN PATENT DOCUMENTS

| CN | 105521788 | | 4/2016 | | |
|---|---|---|---|---|---|
| CN | 105523890 | | 4/2016 | | |
| CN | 10 7285997 | * | 10/2017 | ............ | B01J 23/835 |
| EA | 013588 | | 6/2010 | | |
| EP | 0035720 | | 8/1984 | | |
| RU | 2516702 | | 5/2014 | | |
| RU | 2616620 | | 4/2017 | | |

* cited by examiner

ACID-RESISTANT ALLOY CATALYST

CROSS REFERENCE TO RELATED APPLICATIONS

This application is a national phase application under 35 U.S.C. § 371 of International Application No. PCT/CN2018/092311, filed Jun. 22, 2018, which claims priority to Chinese Patent Application No. 201710481326.4, filed Jun. 22, 2017. The complete disclosure of each of the above-identified applications is fully incorporated herein by reference.

TECHNICAL FIELD

The present invention relates to the technical field of alloy catalysts. In particular, it relates to an acid-resistant alloy catalyst.

BACKGROUND ART

On account of their strong capacity for adsorption of hydrogen, high catalytic activity and thermal stability, Raney nickel alloy catalysts are widely used in many industrial processes and organic synthesis reactions, such as hydrogenation reactions of the unsaturated compounds olefins, alkynes, nitriles, diolefins, aromatic hydrocarbons, carbonyl-containing substances, and even macromolecules having unsaturated bonds, as well as hydrogenation reactions of soluble sugars, such as the hydrogenation of soluble sugars to produce sorbitol and xylitol. Some reactions produce acid in the course of the reaction; in acidic conditions, nickel releases hydrogen to produce nickel ions $Ni^{2+}$, with the result that the catalyst slowly dissolves, losing its hydrogenating activity. In general, it is necessary to add a base to the reaction system to neutralize acid, so as to maintain the stability of the nickel catalyst. The addition of the base will not only increase the cost of base starting material but also increase the cost of product separation and purification, and may even alter the selectivity of the catalyst for the target product. For example, in a reaction in which sugar is hydrocracked directly to prepare ethylene glycol, due to the fact that the sugar undergoes hydrolysis side-reactions very readily in high-temperature aqueous phase conditions, producing small-molecule substances such as acetic acid, lactic acid and formic acid, with a consequent increase in system acidity (Sevilla M, Fuertes A B. Chemical and structural properties of carbonaceous products obtained by hydrothermal carbonization of saccharides. Chemistry—A European Journal. 2009, 15(16): 4195-4203), it is reported in the literature that the stability of a nickel-containing catalyst can be maintained by adjusting the reaction system pH so as to be 7 or more (CN103667365A). However, in high pH conditions, the yield of propylene glycol increases considerably while the yield of ethylene glycol decreases considerably (U.S. Pat. No. 5,107,018, CN101781167A, CN101781171A, CN101781166A); at the same time there is an increase in acids produced in hydrolysis side-reactions, such as formic acid, acetic acid and lactic acid, and the yield of total diols also decreases correspondingly (CN101544537A).

In acidic conditions where the pH<5, reducing sugars are in a relatively stable state, and essentially do not undergo hydrolysis side-reactions (LI Yan, SHEN Canqiu et al., Study of the mechanism of decomposition of sucrose in non-pure sugar solution, China Beet and Sugar, 1996(2): 11-16); thus, the yield of polyols can be increased by running a sugar hydrogenation catalysis system in acidic conditions. However, in low pH conditions, only precious metals such as Ru and Pt are stable, and can serve as catalytically active components. The use of precious metals will considerably increase the production cost of diols. In order to reduce the amount of precious metal used and increase activity, a support with a high specific surface area is generally chosen to fix and disperse same. However, commonly used supports, e.g. inorganic oxides such as alumina, silica and magnesia, are unstable in acidic conditions, readily undergo neutralization reactions, and dissolve in the reaction system, leading to a reduction in the yield of polyols (CN103159587A). Activated carbon, as an acid-resistant material, is also often used as a catalyst support, in order to increase the specific surface area of the catalyst (CN103420796A, CN102643165A, CN102731258A, CN10161325A). However, activated carbon is also unstable in high-temperature hydrogen conditions, readily undergoing a hydrogenation reaction to become methanated (US2002/0169344).

In addition, nickel alloy materials also include Hastelloy, the main composition thereof being Ni 50-64%, Mo 15-30% and Cr 14-21%. This has extraordinary resistance to various chemical industry environments, in particular is resistant to corrosion by various organic acids, and the high molybdenum and chromium contents increase the corrosion resistance thereof. As a corrosion-resistant metal structural material, it is more concerned with guaranteeing mechanical properties.

Thus, there is a need to develop an acid-resistant, cheap and stable nickel alloy catalyst which has no need for a support, can be stably applied in industrial continuous production, and can lower the production cost.

Content of the Invention

An object of the present invention is to provide an acid-resistant alloy catalyst. It can be stably applied in industrial continuous production, and can lower the production cost.

The present invention employs the following technical solution:

An acid-resistant alloy catalyst, comprising nickel, one or more rare earth element, tin, aluminum and molybdenum; in parts by weight, the components are preferably 10-90 parts nickel, 1-5 parts rare earth element, 1-60 parts tin, 5-9 parts aluminum and 0.1-20 parts molybdenum.

The acid-resistant alloy catalyst of the present invention is cheap and stable, and does not need a support.

In this text, the rare earth element is a general designation for 17 chemical elements with atomic numbers 21, 39 and 57-71 in group IIIB of the periodic system, comprising lanthanum (La), Cerium (Ce) and Samarium (Sm), etc.

Furthermore, the acid-resistant alloy catalyst comprises nickel, one or more rare earth element, tin, aluminum, molybdenum and boron or phosphorus; in parts by weight, the components are preferably 10-90 parts nickel, 1-5 parts rare earth element, 1-60 parts tin, 5-9 parts aluminum, 0.1-20 parts molybdenum and 0.01-5 parts boron or phosphorus.

An advantage of using the metal element molybdenum in this catalyst alloy (as compared with the case where nickel, one or more rare earth element, tin and aluminum are included) is that it facilitates the adsorption of reaction starting materials on the catalyst. Reaction starting materials are first of all adsorbed on the molybdenum, and then transferred to the catalytic activity of nickel to undergo a catalytic reaction. At the same time, the addition of molybdenum can keep the aluminum component in the reaction and prevent the loss thereof, thereby guaranteeing the physical strength and service life of the catalyst.

An advantage of avoiding the use of the metal element tungsten in this catalyst alloy (as compared with the case where nickel, one or more rare earth element, tin, aluminum and tungsten are included) is that metal use is reduced by one metal, thereby lowering the cost of catalyst production; compared with a tungsten-containing catalyst alloy, the same catalysis effect can be attained.

For the acid-resistant alloy catalyst of the present invention, chemical reduction or electrolytic deposition may be used to directly prepare an active metal powder having a high specific surface area, or smelting is used first of all to form a metal alloy, then mechanical pulverizing, atomization, etc. are used to form a metal powder, and finally a conventional Raney nickel catalyst activation method is used to form an active metal powder. For example, nickel, a rare earth element, tin, aluminum, molybdenum and boron or phosphorus are added to a smelting furnace in the following parts by weight: 10-90 parts, 1-5 parts, 1-60 parts, 5-9 parts, 0.1-20 parts and 0.01-5 parts respectively; the temperature is increased to 1500-2000° C., then lowered; after thorough mechanical stirring to achieve uniformity, a metal alloy exits the furnace and is obtained. A hammer mill is used to pulverize the metal alloy to a metal powder, and the metal powder is immersed in a 20 wt %-25 wt % aqueous solution of sodium hydroxide for 1-2 hours at 70-95° C., to form an active metal powder having a high specific surface area.

The acid-resistant alloy catalyst of the present invention is used in a process in which a diol is prepared by one-step catalytic hydrocracking of a soluble sugar.

The method uses the sugar and hydrogen as starting materials, which come into contact with a catalyst in water to prepare the diol, the catalyst used being a composite catalyst, composed of a main catalyst and a cocatalyst,
wherein
the main catalyst is the acid-resistant alloy catalyst of the present invention;
the cocatalyst is a soluble tungstic acid salt and/or an insoluble tungsten compound.

Preferably, the diol is ethylene glycol.

The acid-resistant alloy catalyst of the present invention is used as the main catalyst, and used in cooperation with the cocatalyst of the soluble tungstic acid salt and/or insoluble tungsten compound to catalyze the sugar as the composite catalyst in order to obtain the diol; the yield of the diol, in particular ethylene glycol, can be guaranteed at a low production cost. The acid-resistant alloy catalyst of the present invention is stable in acidic conditions, and there is no need to add a base to the reaction system to neutralize acid produced by hydrolysis of sugar. In industrial continuous production, the use of this acid-resistant alloy catalyst as the main catalyst is especially important for the long-term, stable operation of the system and the control of production costs.

Preferably, when ethylene glycol is prepared by the method described above, the pH of the reaction system is 1-7; more preferably, the pH of the reaction system is 3-6. By controlling the system pH so as to be <7, it is not only possible to avoid hydrolysis side-reactions of starting material sugar in the course of the reaction, thereby reducing the consumption of starting material sugar in ethylene glycol production, but the service life of the catalyst is also guaranteed, so the cost of catalyst use can be reduced, and the stability of long-term continuous operation of the reaction system is ensured; at the same time, the ethylene glycol yield is high, while the amount of organic acids and polymers produced is low. If acid produced in the course of the reaction is not sufficient to maintain a low pH, an inorganic acid or an organic acid such as lactic acid, formic acid or acetic acid may be added to the system to adjust the pH of the reaction system. In general, the organic acid or inorganic acid is added together with the starting material sugar.

Preferably, the sugar is selected from one or more of five-carbon monosaccharides, disaccharides and oligosaccharides, six-carbon monosaccharides, disaccharides and oligosaccharides, soluble five-carbon polysaccharides and soluble six-carbon polysaccharides. Original sources of the starting material sugar include but are not limited to sugar-based substances such as beet and sugarcane, starch-based substances such as maize, wheat, barley and cassava, or lignocellulose-based substances such as maize straw, corn cobs, wheat straw, sugarcane bagasse and wood, cellulosic industrial residue such as corn cob residue, or waste paper and waste packaging paper, etc., or polysaccharide substances including seaweed, etc. In this text, soluble five-carbon polysaccharides and soluble six-carbon polysaccharides are five-carbon polysaccharides and six-carbon polysaccharides that are soluble in the reaction conditions of this process, not only five-carbon polysaccharides and six-carbon polysaccharides that are soluble at room temperature.

Preferably, the sugar reacts with hydrogen in the form of an aqueous sugar solution (abbreviated as sugar solution), the aqueous sugar solution having a concentration of 5-60 wt %, more preferably 20-50 wt %. In a continuous operation, the sugar solution may be fed continuously by means of a delivery pump. The use of a suitable catalyst reduces the restrictions of the reaction system with regard to the concentration of starting material sugar; a sugar solution of high concentration can be used as a starting material, and this will greatly reduce the production cost of diols, in particular ethylene glycol, enabling the large-scale and economical production of diols.

Preferably, the soluble tungstic acid salt is one or more of ammonium tungstate, sodium tungstate and sodium phosphotungstate; the insoluble tungsten compound is tungsten trioxide and/or tungstic acid.

The main catalyst is mixed with water and then added to a reactor.

Preferably, the amount of the main catalyst used is 0.01-10 times a sugar feeding amount per hour.

Preferably, the reaction is in a continuous mode.

Preferably, a replenishment amount of the main catalyst is: 0.01-5 kg of main catalyst replenished per 1000 kg of sugar fed. The replenishment of catalyst may be accomplished by discharging a portion of old catalyst through a catalyst discharge valve (generally at the bottom of the reactor) and then replenishing an equal amount of new catalyst through a catalyst feed valve (generally at the bottom of the reactor).

The soluble cocatalyst may be first added to the sugar solution and then added at the same time to the reactor. Preferably, the amount of the soluble cocatalyst used is 0.01-5 wt % of the aqueous sugar solution, more preferably 0.01-2 wt %, and most preferably 0.01-1 wt %.

The insoluble cocatalyst may be added to the reactor together with the main catalyst. Preferably, the amount of the insoluble cocatalyst used is 0.5-50 wt % of the main catalyst, more preferably 5-20 wt %.

Preferably, the reaction pressure of the reaction system is 5-12 MPa, the reaction temperature is 150-260° C., and the reaction time is 10 min.

More preferably, the reaction pressure of the reaction system is 6-10 MPa, the reaction temperature is 180-250° C., and the reaction time is 0.5-3 h. The reaction time is most preferably 0.5-2 hours.

Preferably, the reaction takes place in a slurry bed reactor. In order to ensure the smooth progress of the reaction, the total volume of reaction liquid formed does not exceed 80% of the reactor volume.

Preferably, a filter is provided in the slurry bed reactor, for retaining in the reactor an insoluble part of the catalyst such that the insoluble part is not carried away by reaction liquid and gas flowing out through the filter.

Before the start of the reaction, the main catalyst is added to the slurry bed reactor, hydrogen and sugar solution are separately added simultaneously to the reactor using pumps, and the reaction is carried out; the replenishment of sugar and main catalyst is in a state of continuous flow, and reaction liquid flows out of the reactor continuously. With regard to the cocatalyst, when it is a soluble tungsten compound, it is added to the reactor together with the sugar solution; when it is an insoluble tungsten compound, it is added to the reactor at the same time as the main catalyst. A filter is installed in the reactor. The filter can intercept the catalyst, but gas and reaction liquid will flow out continuously through the filter and enter a condenser to undergo gas/liquid separation. Crude hydrogen undergoes purification to remove $CO$, $CO_2$ and $CH_4$, etc., becoming purified hydrogen again and returning to the reactor. An effluent flowing out of the condenser enters a separation system, and is separated to obtain water, ethylene glycol, propylene glycol, butanediol, glycerol, sorbitol and cocatalyst, etc. Products such as ethylene glycol, propylene glycol and butanediol may be obtained by purification using existing technology (e.g. rectification). Water, sorbitol, glycerol and cocatalyst that is already dissolved in the reaction system are returned to the reactor to react cyclically.

DESCRIPTION OF THE ACCOMPANYING DRAWINGS

Particular embodiments of the present invention are explained in further detail below in conjunction with the accompanying drawings.

PARTICULAR EMBODIMENTS

Figure 1:
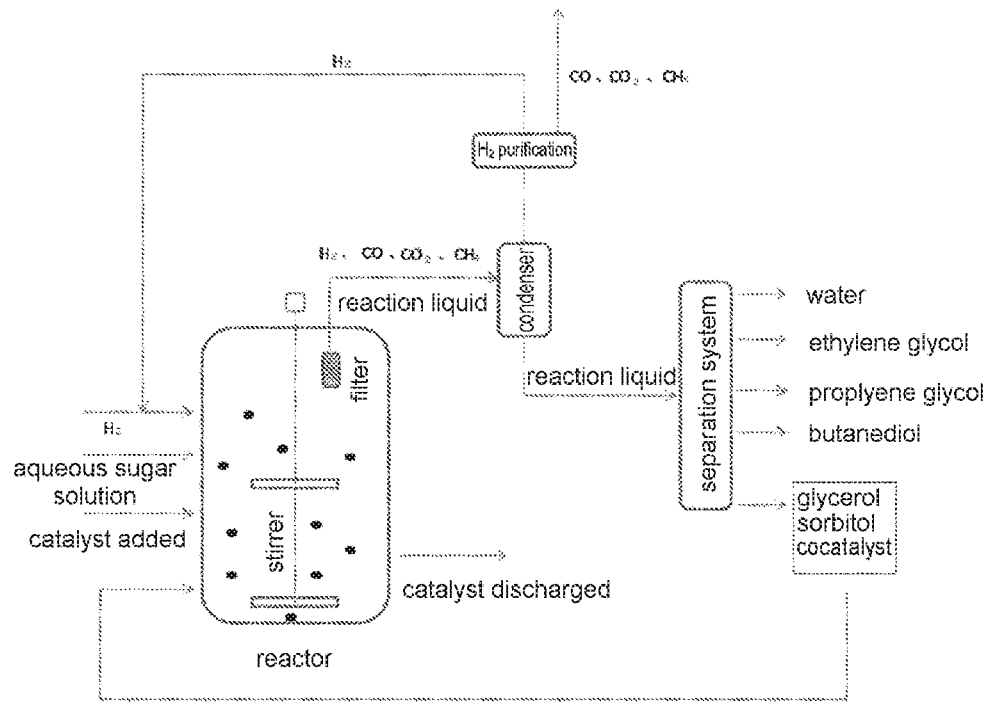
FIG. 1 is a schematic diagram of process flow when the acid-resistant alloy catalyst of the present invention is used in the preparation of a diol by one-step catalytic hydrocracking of a soluble sugar.

In order to explain the present invention more clearly, the present invention is explained further below in conjunction with preferred examples and the accompanying drawings. Those skilled in the art should understand that the content described in specific terms below is explanatory and non-limiting, and should not be used to limit the scope of protection of the present invention.

Example 1

Preparation of Acid-Resistant Alloy Catalyst:

For the acid-resistant alloy catalyst of the present invention, chemical reduction or electrolytic deposition may be used to directly prepare an active metal powder having a high specific surface area, or smelting is used first of all to form a metal alloy, then mechanical pulverizing, atomization, etc. are used to form a metal powder, and finally a conventional Raney nickel catalyst activation method is used to form an active metal powder. For example, nickel, a rare earth element, tin, aluminum, molybdenum and boron or phosphorus are added to a smelting furnace in the following parts by weight: 10-90 parts, 1-5 parts, 1-60 parts, 5-9 parts, 0.1-20 parts and 0.01-5 parts respectively; the temperature is increased to 1500-2000° C., then lowered; after thorough mechanical stirring to achieve uniformity, a metal alloy exits the furnace and is obtained. A hammer mill is used to pulverize the metal alloy to a metal powder, and the metal powder is immersed in a 20 wt %-25 wt % aqueous solution of sodium hydroxide for 1-2 hours at 70-95° C., to form an active metal powder having a high specific surface area.

The following are prepared: an acid-resistant alloy catalyst Ni80Sm1Sn30Al8Mo1 (meaning that the composition of the acid-resistant alloy catalyst is 80 parts Ni+1 part Sm+30 parts Sn+8 parts Al+1 part Mo, likewise below), an acid-resistant alloy catalyst Ni10Sm5Sn3Al2Mo5, an acid-resistant alloy catalyst Ni70Ce1Sn50Al7Mo0.5B5, an acid-resistant alloy catalyst Ni90Ce3Sn60Al9Mo20P0.01 and an acid-resistant alloy catalyst Ni80La1Ce0.5Sn30Al7Mo10.

Example 2

6 L of water and 1400 g of the acid-resistant alloy catalyst Ni80Sm1Sn30Al8Mo1 (as the main catalyst) are added to a 10 L reaction kettle while stirring. The reaction kettle is sealed, and hydrogen is passed in at 1000 L/h at atmospheric pressure to replace air in the reaction kettle for 5 hours, then the hydrogen pressure is increased to 10 MPa, and hydrogen continues to be passed in for 5 hours, the reaction kettle temperature is increased to 250° C., and continuous feeding is begun. The feed composition is: 40 wt % glucose, 0.5 wt % sodium tungstate, 59.5 wt % water, with a sugar solution density of about 1.17 g/cm$^3$; the feeding rate is 3 L/h. The residence time of sugar in the reaction kettle is 2 hours. Acetic acid is added to the reaction kettle such that the reaction system pH is 4.4. Hydrogen and reaction liquid resulting from the reaction flow out of the reaction kettle through a filter and enter a condensing tank, the discharge rate of the reaction liquid being 3 L/h; the reaction liquid is cooled and then discharged from the bottom of the condensing tank, and a liquid effluent is obtained. The liquid effluent enters a rectification separation system; water, ethylene glycol, propylene glycol, glycerol and sorbitol as well as sodium tungstate are obtained separately, wherein a heavy component that is not distilled out, including glycerol and sorbitol as well as sodium tungstate, returns to the reaction system to react cyclically. A sample is taken at the bottom of the condensing tank, and high-efficiency liquid chromatography is used to detect the composition thereof.

High-efficiency liquid chromatography detection may use conventional technology. The present invention provides the following experimental parameters for reference:
  apparatus: Waters 515 HPLC Pump;
  detector: Water 2414 Refractive Index Detector; chromatography column: 300 mm×7.8 mm, Aminex HPX-87H ion exchange column;
  mobile phase: 5 mmol/L sulfuric acid solution;
  mobile phase flow rate: 0.6 ml/min;
  column temperature: 60° C.;
  detector temperature: 40° C.

The results are as follows: glucose conversion is 100%; the diol yield is 85.9%, wherein the ethylene glycol yield is 78%, the propylene glycol yield is 6% and the butanediol yield is 2.1%; the yield of methanol and ethanol is 3.7%, and other yields are 10.4%.

FIG. 1 is a schematic diagram of process flow when the acid-resistant alloy catalyst of the present invention is used in the preparation of a diol by one-step catalytic hydrocracking of a soluble sugar.

Figure 2:
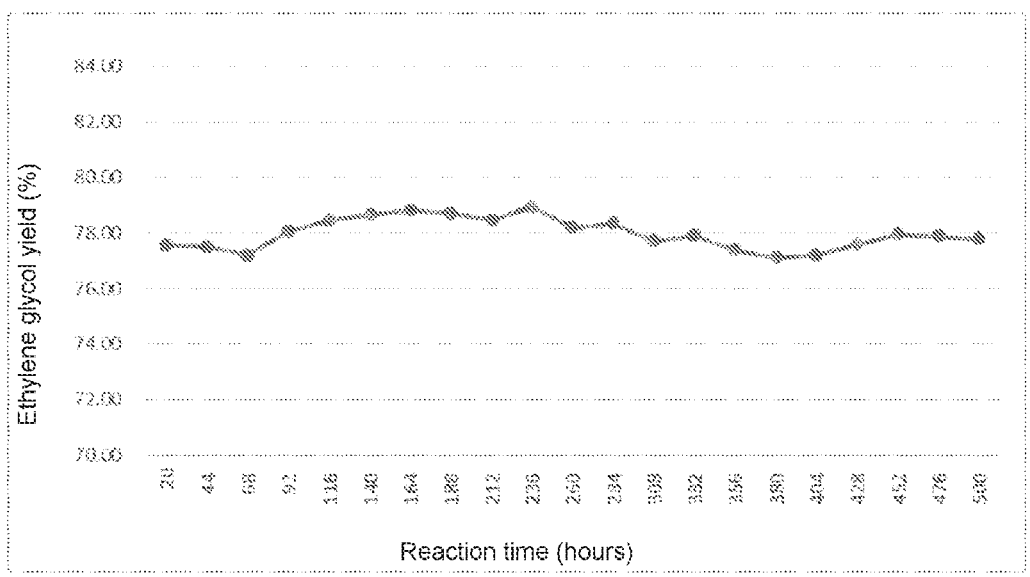
FIG. 2 is a graph of the variation of ethylene glycol yield with time in example 2.

FIG. 2 is a graph of the variation of ethylene glycol yield with reaction system operating time. It can be seen from the figure that the yield of ethylene glycol substantially remains at about 78%. This indicates that the composite catalyst can ensure that after 500 hours of continuous operation of the reaction system, the yield of ethylene glycol is still stable.

Example 3

The acid-resistant alloy catalyst is Ni10Sm5Sn3Al2Mo5, and the amount added is 1400 g.

The feed composition is: 40 wt % glucose, 2 wt % sodium tungstate, 48 wt % water, with a sugar solution density of about 1.17 g/cm$^3$.

Reaction system pH=6.

Other operating conditions are the same as in example 2.

The results are as follows: glucose conversion is 100%; the diol yield is 62.4%, wherein the ethylene glycol yield is 25.4%, the propylene glycol yield is 30.4% and the butanediol yield is 6.6%; the yield of methanol and ethanol is 9.4%, and other yields are 28.2%.

Example 4

The acid-resistant alloy catalyst is Ni70Ce1Sn50Al7Mo0.5B5, and the amount added is 500 g. 100 g of tungsten trioxide is added.

The feed composition is: 60 wt % glucose, 40 wt % water, with a sugar solution density of about 1.29 g/cm$^3$.

Reaction system pH=4.2.

Other operating conditions are the same as in example 2.

The results are as follows: glucose conversion is 100%; the diol yield is 20.8%, wherein the ethylene glycol yield is 10.9%, the propylene glycol yield is 7.5% and the butanediol yield is 2.4%; the yield of methanol and ethanol is 15.6%, and other yields are 63.6%.

Example 5

The acid-resistant alloy catalyst is Ni90Ce3Sn60Al9Mo20P0.01, and the amount added is 1000 g.

The feed composition is: 15 wt % xylose, 40 wt % glucose, 1 wt % maltobiose, 1 wt % maltotriose, 1 wt % sodium phosphotungstate, 42 wt % water, with a sugar solution density of about 1.22 g/cm$^3$.

Reaction system pH=4.8.

Other operating conditions are the same as in example 2.

The results are as follows: conversion of xylose, glucose, maltobiose and maltotriose is 100%; the diol yield is 71.6%, wherein the ethylene glycol yield is 65.5%, the propylene glycol yield is 4.3% and the butanediol yield is 1.8%; the yield of methanol and ethanol is 3.4%, and other yields are 25%. After 500 hours of operation of the catalyst, the yield of ethylene glycol is still stable.

Example 6

The acid-resistant alloy catalyst is Ni80La1Ce0.5Sn30Al7Mo10, and the amount added is 5000 g.

The feed composition is: 50 wt % xylose, 0.1 wt % sodium tungstate, 49.9 wt % water, with a sugar solution density of about 1.21 g/cm$^3$.

Reaction system pH=4.8.

Other operating conditions are the same as in example 2.

The results are as follows: xylose conversion is 100%; the diol yield is 72.1%, wherein the ethylene glycol yield is 58.8%, the propylene glycol yield is 12.4% and the butanediol yield is 0.9%; the yield of methanol and ethanol is 6.9%, and other yields are 21%. After 500 hours of operation of the catalyst, the yield of ethylene glycol is still stable.

Example 7

The acid-resistant alloy catalyst is Ni80Sm1Sn30Al8Mo1, and the amount added is 1400 g.

The feed composition is: 40 wt % sucrose, 1 wt % sodium tungstate, 59 wt % water, with a sugar solution density of about 1.18 g/cm$^3$.

Reaction system pH=4.7.

Other operating conditions are the same as in example 2.

The results are as follows: sucrose conversion is 100%; the diol yield is 81.7%, wherein the ethylene glycol yield is 52.6%, the propylene glycol yield is 24% and the butanediol yield is 5.1%; the yield of methanol and ethanol is 3.3%, and other yields are 15%. After 500 hours of operation of the catalyst, the yield of ethylene glycol is still stable.

Clearly, the above examples of the present invention are merely examples given in order to clearly explain the present invention, and do not limit the embodiments of the present invention. Other changes or modifications in different forms may still be made on the basis of the description above. It is not possible to exhaustively list all embodiments here. All obvious changes or modifications derived from the technical solution of the present invention still fall within the scope of protection of the present invention.

The invention claimed is:

1. An acid-resistant alloy catalyst, characterized in that the acid-resistant alloy catalyst comprises nickel, one or more rare earth element, tin, aluminum and molybdenum, wherein the catalyst does not contain tungsten.

2. The acid-resistant alloy catalyst as claimed in claim 1, characterized in that the acid-resistant alloy catalyst comprises, in parts by weight, 10-90 parts nickel, 1-5 parts rare earth element, 1-60 parts tin, 5-9 parts aluminum and 0.1-20 parts molybdenum.

3. The acid-resistant alloy catalyst as claimed in claim 1, characterized in that the acid-resistant alloy catalyst comprises nickel, one or more rare earth element, tin, aluminum, molybdenum and boron or phosphorus.

4. The acid-resistant alloy catalyst as claimed in claim 3, characterized in that the acid-resistant alloy catalyst comprises, in parts by weight, 10-90 parts nickel, 1-5 parts rare earth element, 1-60 parts tin, 5-9 parts aluminum, 0.1-20 parts molybdenum and 0.01-5 parts boron or phosphorus.

5. The acid-resistant alloy catalyst as claimed in claim 1, characterized in that the rare earth element is a general designation for 17 chemical elements with atomic numbers 21, 39 and 57-71 in group IIIB of the periodic system.

* * * * *